United States Patent
Yamada

(10) Patent No.: US 8,034,917 B2
(45) Date of Patent: Oct. 11, 2011

(54) PRIMER-DIRECTED CHROMOSOME PAINTING

(75) Inventor: N. Alice Yamada, San Jose, CO (US)

(73) Assignee: Agilent Technologies, Inc., Santa Clara, CA (US)

( * ) Notice: Subject to any disclaimer, the term of this patent is extended or adjusted under 35 U.S.C. 154(b) by 354 days.

(21) Appl. No.: 12/200,675

(22) Filed: Aug. 28, 2008

(65) Prior Publication Data

US 2010/0055681 A1 Mar. 4, 2010

(51) Int. Cl.
*C07H 21/04* (2006.01)
*C12P 19/34* (2006.01)

(52) U.S. Cl. .................. 536/24.31; 536/24.33; 435/6.12; 435/91.2

(58) Field of Classification Search .......................... None
See application file for complete search history.

(56) References Cited

OTHER PUBLICATIONS

Knutsen, T., et al. The interactive online SKY/M-FISH & CGH database and the entrez cancer chromosomal aberrations with the genome sequence. Genes Chromosomes Cancer. 2005, vol. 44, No. 1, pp. 52-64.

Muller, S., et al. Toward a multicolor chromosome bar code for the entire human karyotype by fluorescence in situ hybridization. Human Genetics. 1997, vol. 100, pp. 271-278.

Ried, T., et al. Chromosome painting: a useful art. Human Molecular Genetics. 1998, vol. 7, No. 10, pp. 1619-1626.

Une, T., et al. Assessment of molecular cytogenetic methods for the detection of chromosomal abnormalities. Acta Medica Okayama. 2006, vol. 60, No. 5, pp. 279-287.

Wu, H., et al. Delineation of an isodicentric Y chromosome in a mosaic 45,X/46,X,idic(Y)(qter-p11.3::p11.3-qter) fetus by SRY sequencing, G-banding, FISH, SKY and study of distribution in different tissues. Journal of the Formosan Medical Association. 2007, vol. 106, No. 5, pp. 403-410.

*Primary Examiner* — Samuel Woolwine
(74) *Attorney, Agent, or Firm* — James S. Keddie; Bret E. Field; Bozicevic, Field & Francis

(57) ABSTRACT

An oligonucleotide composition is provided. The subject composition comprises: a mixture of at least 10 of sets of oligonucleotides, wherein each of the sets of oligonucleotides comprises at least 100 different oligonucleotides of the following formula: $X_1$—V—$X_2$, wherein: $X_1$ and $X_2$ provide binding sites for a pair of PCR primers and V is a variable region that has a variable nucleotide sequence that is complementary to one or more discrete regions of a mammalian genome; the nucleotide sequences of $X_1$ and $X_2$ are the same for each oligonucleotide of a set and different for oligonucleotides of different sets; and the variable regions of each set are complementary to different discrete regions of said mammalian genome. Methods of using the composition and kits containing the composition are also provided.

19 Claims, 1 Drawing Sheet

PRIMER-DIRECTED CHROMOSOME PAINTING

BACKGROUND

Chromosomal rearrangements are a type of genomic variation, which have been long been associated with genetic diseases such as Down syndrome (a trisomy), Jacobsen syndrome (a deletion) and Burkitt's lymphoma (a translocation) and have traditionally been studied via karyotype analysis. Genomic instability also leads to complex patterns of chromosomal rearrangements in certain cells, such as, for example, cancer cells.

Standard cytogenetic assays such as Giemsa (G) banding have identified numerous cancer-specific translocations and chromosomal abnormalities in cancer cells such as the Philadelphia (t9,22) chromosome. Improvements in cytogenetic banding and visualization such as M banding and spectral karyotyping (SKY) have enabled detailed analyses on a chromosome by chromosome basis of inversions and translocations, as well as the identification of regions of loss in cancers of interest. Fluorescence in situ hybridization (FISH) further allows for the detection of the presence or absence of specific DNA sequences on chromosomes by using fluorescent probes that bind to only those parts of the chromosome with which they show a high degree of complementarity. All of these methods, however, have limited resolution since probes are generated from large pieces of DNA (flow-sorted chromosomes or bacterial artificial chromosomes for SKY and FISH, respectively). Because these probes are generated over very large regions of the genome, microtranslocations and microinversions cannot be resolved by current methods. The large templates from which probes are generated also present another disadvantage, in that both SKY and FISH probes contain repetitive DNA elements that are inherent in the large template DNA fragments. Thus, there has been an increasing need to understand more subtle chromosomal defects with substantially improved resolution, and without a priori knowledge of their location. A large unmet need exists to develop technical methods that detect novel, specific chromosomal abnormalities.

In one aspect, there is a need to avoid non-specific amplification of starting probes, which can lead to random amplification bias. There is also a need to create probes of a designated length consistently as fragments generated in current PCR processes are often too long to be used effectively in FISH, such that they require partial digestion by restriction enzymes which is difficult to control. There is also a need to target chromosomal regions by color on a very fine level such that microduplications, microinversions and microdeletions can be detected. Current techniques allow for painting of chromosomes in sections, however, the smallest unit that can be painted in one color is 10 megabases. There is also a need for utilization of standard laboratory equipment for the visual detection of signals from labeled probes such that special filters, software and processing steps are not required.

Certain aspects of this disclosure address these needs and describe methods and kits for practicing the same.

SUMMARY

An oligonucleotide composition is provided. The subject composition comprises: a mixture of at least two sets of oligonucleotides, wherein each of the sets of oligonucleotides comprises at least 10 different oligonucleotides of the following formula: $X_1$—V—$X_2$, wherein: $X_1$ and $X_2$ are binding sites for a pair of PCR primers and V is a variable region that has a variable nucleotide sequence that is complementary to one or more discrete regions of a mammalian genome; the nucleotide sequences of $X_1$ and $X_2$ are the same for each oligonucleotide of a set and different for oligonucleotides of different sets; and the variable regions of each set are complementary to different discrete regions of said mammalian genome. Methods of using the composition and kits containing the composition are also provided.

DEFINITIONS

Figure 1:
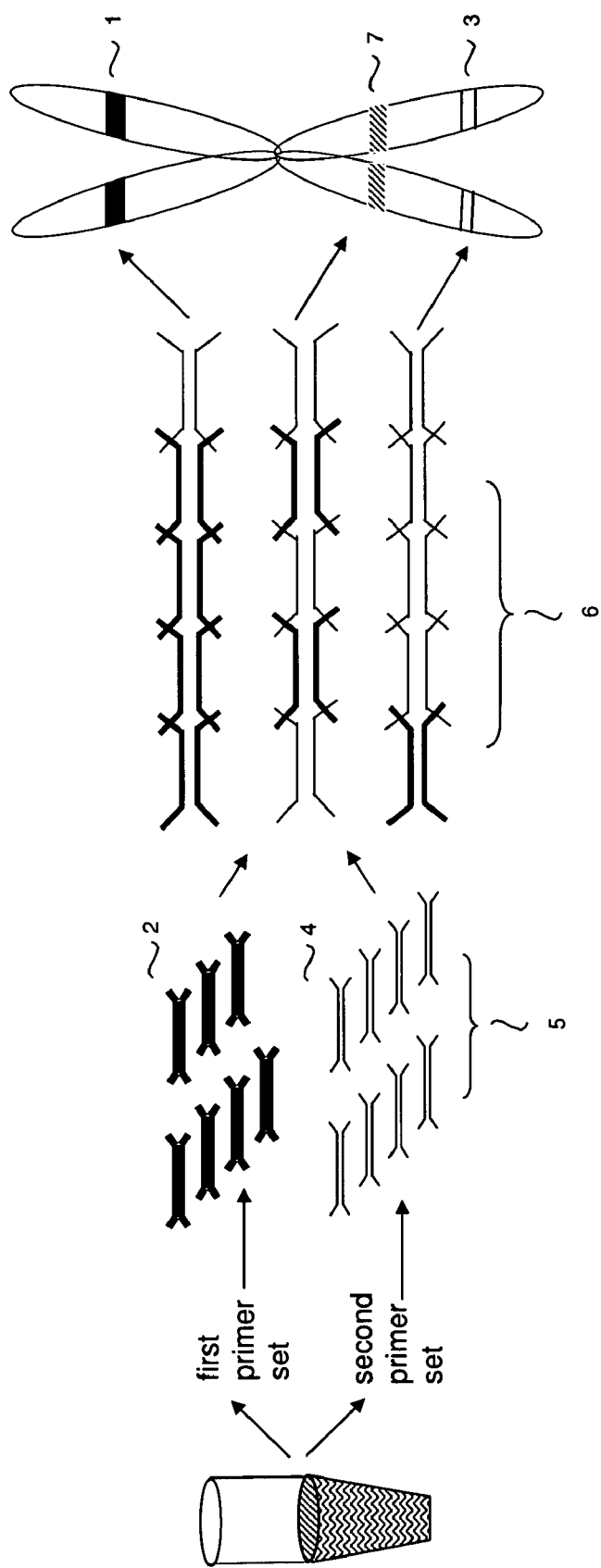
FIG. 1 schematically illustrates certain features of one embodiment of the method described herein.

The term "sample" as used herein relates to a material or mixture of materials, typically, although not necessarily, in liquid form, containing one or more analytes of interest.

The term "genomic sample" as used herein relates to a material or mixture of materials, containing genetic material from an organism. The term "genomic DNA" as used herein refers to deoxyribonucleic acids that are obtained from an organism. The terms "genomic sample" and "genomic DNA" encompass genetic material that may have undergone amplification, purification, or fragmentation. The term "test genome," as used herein refers to genomic DNA that is of interest in a study.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, are functionalized as ethers, amines, or the likes.

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine and thymine (G, C, A and T, respectively).

The term "oligonucleotide" as used herein denotes a single stranded multimer of nucleotide of from about 2 to 200 or more, up to about 500 nucleotides or more. Oligonucleotides may be synthetic or may be made enzymatically, and, in some embodiments, are less than 10 to 50 nucleotides in length. Oligonucleotides may contain ribonucleotide monomers (i.e., may be oligoribonucleotides) or deoxyribonucleotide monomers. Oligonucleotides may be 10 to 20, 11 to 30, 31 to 40, 41 to 50, 51-60, 61 to 70, 71 to 80, 80 to 100, 100 to 150 or 150 to 200 nucleotides in length, for example.

The term "primer" as used herein refers to an oligonucleotide that has a nucleotide sequence that is complementary to a region of a target nucleic acid. A primer binds to the complementary region and is extended, using the target nucleic acid as the template, under primer extension conditions. A primer may be in the range of about 15 to about 60 nucleotides although primers outside of this length are envisioned.

The term "PCR conditions" as used herein refers to conditions suitable for polymerase chain reaction and include incubating a nucleic acid with two primers, nucleotides, a thermostable polymerase and a buffer for a period of time at certain temperatures. Such conditions are well known in the art. The resulting products produced by PCR are referred herein as "amplification products."

The term "amplifying" as used herein refers to generating one or more copies of a target nucleic acid, using the target nucleic acid as a template.

The term "sequence-specific oligonucleotide" as used herein refers to an oligonucleotide that only binds to a single site in a haploid genome. In certain embodiments, a "sequence-specific" oligonucleotide may hybridize to a complementary nucleotide sequence that is unique in a sample under study.

The term "complementary" as used herein refers to a nucleotide sequence that base-pairs by non-covalent bonds to a target nucleic acid of interest. In the canonical Watson-Crick base pairing, adenine (A) forms a base pair with thymine (T), as does guanine (G) with cytosine (C) in DNA. In RNA, thymine is replaced by uracil (U). As such, A is complementary to T and G is complementary to C. In RNA, A is complementary to U and vice versa. Typically, "complementary" refers to a nucleotide sequence that is fully complementary to a target of interest such that every nucleotide in the sequence is complementary to every nucleotide in the target nucleic acid in the corresponding positions. In certain cases, a nucleotide sequence may be partially complementary to a target, in which not all nucleotide is complementary to every nucleotide in the target nucleic acid in all the corresponding positions.

The term "probe," as used herein, refers to a nucleic acid that is complementary to a nucleotide sequence of interest. In certain cases, detection of a target analyte requires hybridization of a probe to a target. In certain embodiments, a probe may be immobilized on a surface of a substrate, where the substrate can have a variety of configurations, e.g., a sheet, bead, or other structure. In certain embodiments, a probe may be present on a surface of a planar support, e.g., in the form of an array.

An "array," includes any two-dimensional or substantially two-dimensional (as well as a three-dimensional) arrangement of addressable regions, e.g., addressable regions, e.g., spatially addressable regions or optically addressable regions, bearing nucleic acids, particularly oligonucleotides or synthetic mimetics thereof, and the like. Where the arrays are arrays of nucleic acids, the nucleic acids may be adsorbed, physisorbed, chemisorbed, or covalently attached to the arrays at any point or points along the nucleic acid chain.

Any given substrate may carry one, two, four or more arrays disposed on a surface of the substrate. Depending upon the use, any or all of the arrays may be the same or different from one another and each may contain multiple spots or features. An array may contain one or more, including more than two, more than ten, more than one hundred, more than one thousand, more ten thousand features, more than one hundred thousand features, or even more than million features, in an area of less than 20 $cm^2$ or even less than 10 $cm^2$, e.g., less than about 5$cm^2$, including less than about 1 $cm^2$, less than about 1 $mm^2$, e.g., 100 $\mu m^2$, even smaller. For example, features may have widths (that is, diameter, for a round spot) in the range from a 10 µm to 1.0 cm. In other embodiments each feature may have a width in the range of 1.0 µm to 1.0 mm, usually 5.0 µm to 500 µm, and more usually 10 µm to 200 µm. Non-round features may have area ranges equivalent to that of circular features with the foregoing width (diameter) ranges. At least some, or all, of the features are of different compositions (for example, when any repeats of each feature composition are excluded the remaining features may account for at least 5%, 10%, 20%, 50%, 95%, 99% or 100% of the total number of features). Inter-feature areas will typically (but not essentially) be present which do not carry any nucleic acids (or other biopolymer or chemical moiety of a type of which the features are composed). Such inter-feature areas typically will be present where the arrays are formed by processes involving drop deposition of reagents but may not be present when, for example, photolithographic array fabrication processes are used. It will be appreciated though, that the inter-feature areas, when present, could be of various sizes and configurations.

Each array may cover an area of less than 200 $cm^2$, or even less than 50 $cm^2$, 5 $cm^2$, 1 $cm^2$, 0.5 $cm^2$, or 0.1 $cm^2$. In certain embodiments, the substrate carrying the one or more arrays will be shaped generally as a rectangular solid (although other shapes are possible), having a length of more than 4 mm and less than 150 mm, usually more than 4 mm and less than 80 mm, more usually less than 20 mm; a width of more than 4 mm and less than 150 mm, usually less than 80 mm and more usually less than 20 mm; and a thickness of more than 0.01 mm and less than 5.0 mm, usually more than 0.1 mm and less than 2 mm and more usually more than 0.2 mm and less than 1.5 mm, such as more than about 0.8 mm and less than about 1.2 mm.

Arrays can be fabricated using drop deposition from pulse-jets of either precursor units (such as nucleotide or amino acid monomers) in the case of in situ fabrication, or the previously obtained nucleic acid. Such methods are described in detail in, for example, the previously cited references including U.S. Pat. Nos. 6,242,266, 6,232,072, 6,180,351, 6,171,797, 6,323,043, U.S. patent application Ser. No. 09/302,898 filed Apr. 30, 1999 by Caren et al., and the references cited therein. As already mentioned, these references are incorporated herein by reference. Other drop deposition methods can be used for fabrication, as previously described herein. Also, instead of drop deposition methods, photolithographic array fabrication methods may be used. Inter-feature areas need not be present particularly when the arrays are made by photolithographic methods as described in those patents.

Arrays may also be made by distributing pre-synthesized nucleic acids linked to beads, also termed microspheres, onto a solid support. In certain embodiments, unique optical signatures are incorporated into the beads, e.g. fluorescent dyes, which could be used to identify the chemical functionality on any particular bead. Since the beads are first coded with an optical signature, the array may be decoded later, such that correlation of the location of an individual site on the array with the probe at that particular site may be made after the array has been made. Such methods are described in detail in, for example, U.S. Pat. Nos. 6,355,431, 7,033,754, and 7,060,431.

An array is "addressable" when it has multiple regions of different moieties (e.g., different oligonucleotide sequences) such that a region (i.e., a "feature" or "spot" of the array) at a particular predetermined location (i.e., an "address") on the array contains a particular sequence. Array features are typically, but need not be, separated by intervening spaces. An array is also "addressable" if the features of the array each have an optically detectable signature that identifies the moiety present at that feature.

The terms "determining", "measuring", "evaluating", "assessing", "analyzing", and "assaying" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

The term "using" has its conventional meaning, and, as such, means employing, e.g., putting into service, a method or composition to attain an end. For example, if a program is used to create a file, a program is executed to make a file, the file usually being the output of the program. In another example, if a computer file is used, it is usually accessed, read, and the information stored in the file employed to attain an end. Similarly if a unique identifier, e.g., a barcode is used, the unique identifier is usually read to identify, for example, an object or file associated with the unique identifier.

The term "chromosomal rearrangement," as used herein, refers to an event where one or more parts of a chromosome are rearranged within a single chromosome or between chromosomes. In certain cases, a chromosomal rearrangement may reflect an abnormality in chromosome structure. A chromosomal rearrangement may be an inversion, a deletion, an insertion or a translocation, for example.

The term "contacting" means to bring or put together. As such, a first item is contacted with a second item when the two items are brought or put together, e.g., by touching them to each other or combining them in the same solution. Thus, a "contacted sample" is a test chromosome onto which oligonucleotide probes have been hybridized.

The term "hybridization" refers to the specific binding of a nucleic acid to a complementary nucleic acid via Watson-Crick base pairing. Accordingly, the term "in situ hybridization" refers to specific binding of a nucleic acid to a metaphase or interphase chromosome.

The terms "hybridizing" and "binding", with respect to nucleic acids, are used interchangeably.

The terms "plurality", "set" or "population" are used interchangeably to mean at least 2, at least 10, at least 100, at least 500, at least 1000, at least 10,000, at least 100,000, at least 1000,000, at least 10,000,000 or more.

The term "chromosomal region" as used herein denotes a contiguous length of nucleotides in a genome of an organism. A chromosomal region may be in the range of 10 kb in length to an entire chromosome, e.g., 100 kb to 10 MB for example.

A "test chromosome" is an intact metaphase or interphase chromosome isolated from a mammalian cell. An intact chromosome contains a centromere, a long arm containing a telomere and a short arm containing a telomere. A test chromosome may contain an inversion, translocation, deletion insertion, or other rearrangement relative to a reference chromosome. A test chromosome is the chromosome under study.

A "reference chromosome" is an intact metaphase chromosome to which a test chromosome may be compared to identify a rearrangement. A reference chromosome may be arbitrarily chosen. A reference chromosome may have a known sequence. A reference chromosome may itself contain a chromosomal rearrangement.

The term "reference chromosomal region," as used herein refers to a chromosomal region to which a test chromosomal is compared. In certain cases, a reference chromosomal region may be of known nucleotide sequence, e.g., a chromosomal region whose sequence is deposited at NCBI's Genbank database or other database, for example.

The term "in situ hybridization conditions" as used herein refers to conditions that allow hybridization of a nucleic acid to a complementary nucleic acid in an intact chromosome. Suitable in situ hybridization conditions may include both hybridization conditions and optional wash conditions, which include temperature, concentration of denaturing reagents, salts, incubation time, etc. Such conditions are known in the art.

"Distinct non-contiguous regions" refers to regions or intervals on a chromosome that are not contiguous.

A "binding pattern" refers to the pattern of binding of a set of labeled probes to an intact chromosome.

DESCRIPTION OF EXEMPLARY EMBODIMENTS

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Oligonucleotide Compositions

As noted above, an oligonucleotide composition is provided. In certain embodiments, the composition comprises a mixture of at least 5 of sets of oligonucleotides, e.g., at least 2, at least 10, at least 50, at least 100 up to 100 or more, where each of the sets of oligonucleotides contains at least 10 different oligonucleotides of the following formula $X_1$—V—$X_2$ (from 5' to 3'), where $X_1$ and $X_2$ provide binding sites for a pair of PCR primers (e.g., where $X_1$ has the same sequence as a first PCR primer and $X_2$ has a sequence that is complementary to a second PCR primer), and V is a variable region that has a variable nucleotide sequence that is complementary to one or more discrete regions of a mammalian genome. The variable region may be amplified by the pair of PCR primers.

Within each set of primers, the nucleotide sequences of $X_1$ and $X_2$ are the same such that all of the variable regions of a single set of oligonucleotides can be amplified with a single pair of different PCR primers. However, between each set, the nucleotide sequences of $X_1$ and $X_2$ are different such that the variable regions of each set of oligonucleotides can only be amplified with a single pair of PCR primers. For example, the variable regions of one set may be amplified with a first pair of PCR primers, and the variable regions of another set may be amplified using a second pair of PCR primers, etc.

The variable regions of the oligonucleotides of each set are complementary to different discrete regions of the mammalian chromosome such that the amplification products made using each set of oligonucleotides may hybridize to one or more regions of the mammalian chromosome. In certain embodiments, the variable regions of a single set of oligonucleotides may all be complementary to the same region of the chromosome. In other embodiments, the variable regions of a single set of oligonucleotides may be complementary to different regions of a chromosome (e.g., in the example shown in FIG. 1). The variable regions of the different oligonucleotides within each set of oligonucleotides probes are different from one another, and specifically bind only one site in a genome under study.

As will be described in greater detail below, the oligonucleotide compositions described herein may be employed in a variety of chromosomal labeling methods that generally include amplifying the variable regions from a first set of oligonucleotides using a first primer pair and amplifying the variable regions from a second set of oligonucleotides using a second primer pair. The different products can be labeled with different labels that are distinguishable from one another (e.g., different fluorescent labels), and hybridized to a sample that comprises an intact chromosome. The pattern of binding of the oligonucleotides on the chromosome can then be analyzed.

In certain cases, the variable regions amplified from the first and second sets of oligonucleotides may bind to different regions of the chromosome, in which case the different regions of the chromosome can be identified by the signal associated therewith. In other cases, some of the variable regions amplified from the first and second sets of oligonucleotides may bind to the same region of the chromosome, in which case a composite signal may be produced. The composite signal may indicate the identity of the chromosomal region. In certain embodiments, the ratio of the magnitudes of the signals from the labels associated with the chromosomal region (e.g., the ratio of the magnitude of two different wavelengths of fluorescence) may indicate the identity of the chromosomal region. In other embodiments, the identity of the chromosomal region may be indicated by a composite signal that contains two or more different signals that are unique to that region. In the example shown in FIG. 1, two sets of oligonucleotides are amplified. The first set is labeled using one label (shown in dark lines), and the second set is labeled using another label (shown in thin lines). The labeled amplification products are combined and hybridized with an intact chromosome to produce a binding pattern in which different regions of the chromosome can be distinguished by the ratios of the magnitude of the different labels at the different regions. In the example shown, one region produces a composite signal that is 80% one label and 20% the other label (illustrated as 80% thick lines and 20% thin lines); another region is 50% one label and 50% the other label, and another region is 20% one label and 80% the other label. The different regions of the chromosome can thus be uniquely identified.

Each set of oligos of the oligonucleotide composition comprises at least 10, at least 100, at least 1000, e.g. at least 5,000, at least 10,000 or at least 50,000, up to 100,000 or more different oligonucleotides, where, in certain embodiments, the oligonucleotides may be in the range of 100 to 200 nucleotides in length, or more. The primer binding sites may be 15-40 (e.g., 18 to 30) nucleotides in length, and the variable region may be in the range of 30 to 100 (e.g., 40-80) nucleotides in length, although primer binding sites and variable regions outside of these ranges are envisioned. In certain cases, the variable regions may overlap with the variable regions of other probes or may be uniquely tiled (e.g. end-to-end tiling). The extent of overlap may be anywhere from 10% to 90% overlap.

Since the genome sequences of many organisms, including many bacteria, fungi, plants and animals, e.g., mammals such as human, primates, and rodents such as mouse and rat, are known and some are publicly available (e.g., in NCBI's Genbank database), the design of the above-described oligonucleotides is within the skill of one of skilled in the art. In particular embodiments, the variable domains of the oligonucleotides may be designed using methods set forth in US20040101846, U.S. Pat. No. 6,251,588, US20060115822, US20070100563, US20080027655, US20050282174, U.S. patent application Ser. No. 11/729,505, filed March 2007 and U.S. patent application Ser. No. 11/888,059, filed Jul. 30, 2007 and references cited therein, for example., In certain embodiments, the oligonucleotides may be synthesized in an array using in situ synthesis methods in which nucleotide monomers are sequentially added to a growing nucleotide chain that is attached to a solid support in the form of an array. Such in situ fabrication methods include those described in U.S. Pat. Nos. 5,449,754 and 6,180,351 as well as published PCT application no. WO 98/41531, the references cited therein, and in a variety of other publications. In one embodiment, the oligonucleotide composition may be made by fabricating an array of the oligonucleotides using in situ synthesis methods, and cleaving oligonucleotides from the array.

The oligonucleotide composition may be an aqueous composition (i.e., the oligonucleotides are dissolved in a water-based medium), or the oligonucleotides composition may be a dry composition, where the oligonucleotides may be in the form of a dry pellet.

Methods for Sample Analysis

A labeling method and a method of sample analysis are also provided. In general terms, the labeling method involves contacting the above-described oligonucleotide composition with a first pair of PCR primers under PCR conditions to provide a first set of amplification products, where the first amplification products contains the amplified variable regions of a first set of oligonucleotides; and then labeling the first amplification products to provide first labeled amplification products. These products may be hybridized with an intact chromosome under in situ hybridization conditions, and a binding pattern identified. In certain embodiments, the first amplification products may be labeled with a single label (e.g., a single type of fluorophore) that identifies the chromosomal regions to which the labels bind. In other embodiments, the first amplification products are labeled with a plurality (e.g., two or three fluorophores) to provide a composite signal (e.g., a signal containing two or more different wavelengths of light) that distinguishes it from other signals.

In certain cases, the method may further involve contacting the above-described oligonucleotide composition with a second pair of PCR primers under PCR conditions to provide a second set of amplification products, where the second set of amplification products contain the variable regions of a second set of oligonucleotides. Further sets of amplification products may be amplified using further pairs of PCR primers. As many amplification products may be amplified as needed. For example, at least 2, at least 10, at least 50, at least 100, or at least 1,000 or 10,000 or more pairs of primers may be employed to amplify a corresponding number of products. While these amplification reactions may be done separately, in certain embodiments they may be multiplexed.

The first and second labeled amplification products may be differentially labeled such that the signal from a chromosomal region hybridized to the first labeled amplification products is distinguishable from the signal obtained from a chromosomal region hybridized to the second labeled amplification products. In one embodiment, the first and second amplification products are labeled with different labels, e.g., two different fluorophores (as shown in FIG. 1), and the chromosomal region bound by first and second amplification products produces composite signal that identifies the region. As would be readily apparent, the first and second amplification products may bind many different, non-overlapping regions of a chromosome or on many chromosomes. Binding of the first and second amplification products to those regions indicates the identity of the regions. In certain cases, a portion of the amplification products from the first amplification products may bind to the same chromosomal regions as a portion of the second amplification products, in which case three distinct chromosomal regions may be identified (one region associated with only the first label, another region associated with only the second label, and another region associated with a both labels). As noted above and shown in FIG. 1, the identity of the regions containing a mixture of labels can be further determined by analyzing the ratio of the magnitude of the different signal associated with those regions.

In greater detail and with further reference to FIG. 1, certain embodiments of the method include identifying blocks of genomic regions 1, 3, and 7 to be "painted" with specific fluorophores. Each such region will be painted with labeled amplification products. The labeled amplification products may be amplified from fragments with primer sequences that dictate which genomic regions are to be colored with which specific fluorophores. For example, all regions of the genome to be labeled with fluorophore A, shown here as 1, are synthesized as oligonucleotides flanked by primer sequences A, shown here as 2. Other regions of the genome to be labeled with fluorophore B, shown here as 3, will be synthesized with flanking primer sequences B, shown here as 4. The oligonucleotides will be amplified by polymerase chain reaction (PCR), and each pool of oligonucleotides with a designated primer sequence will be labeled with a specific fluorophore corresponding to that primer sequence.

Labels may be incorporated into the amplification products by any of a number of means well known to those of skill in the art. For example, the label may be simultaneously incorporated during the amplification step. Thus, for example, polymerase chain reaction (PCR) with labeled primers or labeled nucleotides will provide a labeled amplification product. In certain embodiments, a label may be added directly to the amplification products. Means of attaching labels to nucleic acids are well known to those of skill in the art and include, for example nick translation or end-labeling, by kinasing of the nucleic acid and subsequent attachment of a nucleic acid linker joining the oligonucleotides to a label. Standard methods may be used for labeling the oligonucleotide, for example, as set out in Ausubel, et al, (*Short Protocols in Molecular Biology,* 3rd ed., Wiley & Sons, 1995) and Sambrook, et al, (*Molecular Cloning: A Laboratory Manual,* Third Edition, (2001) Cold Spring Harbor, N.Y.).

In general terms, once labeled, the amplification products are hybridized to a sample containing intact chromosomes, and the binding pattern analyzed. For example, an interphase or metaphase chromosome preparation may be produced. The chromosomes are attached to a substrate, e.g., glass. The probe is then applied to the chromosome DNA and incubated under hybridization conditions. Wash steps remove all unhybridized or partially-hybridized probes, and the results are visualized and quantified using a microscope that is capable of exciting the dye and recording images.

Such methods are generally known in the art and may be readily adapted for use herein. For example, the following references discuss chromosome hybridization: Ried et al., *Chromosome painting: a useful art* Human Molecular Genetics, Vol 7, 1619-1626; Speicher et al: Karyotyping human chromosomes by combinatorial multi-fluor FISH, Nature Genetics, 12, 368-376, 1996; Schröck et al: Multicolor Spectral Karyotyping of Human Chromosomes. Science, 494-497, 1996; Griffin et al Molecular cytogenetic characterization of pancreas cancer cell lines reveals high complexity chromosomal alterations. Cytogenet Genome Res. 2007;118 (2-4):148-56; Peschka et al, Analysis of a de novo complex chromosome rearrangement involving chromosomes 4, 11, 12 and 13 and eight breakpoints by conventional cytogenetic, fluorescence in situ hybridization and spectral karyotyping. Prenat Diagn. 1999 December; 19(12):1143-9; Hilgenfeld et al, Analysis of B-cell neoplasias by spectral karyotyping (SKY). Curr Top Microbiol Immunol. 1999;246:169-74. Ried et al, Genomic changes defining the genesis, progression, and malignancy potential in solid human tumors: a phenotype/genotype correlation. Genes Chromosomes Cancer. 1999 July;25(3):195-204; and Agarwal et al, Comparative genomic hybridization analysis of human parathyroid tumors. Cancer Genet Cytogenet. 1998 Oct. 1; 106(1):30-6.

Each resultant amplification product is labeled with a fluorphore that is different from the fluorophore used to label other amplification products. This allows for fine-tune control over which probe is labeled with which fluorophore. In this sense, the primer sequences used to amplify the starting oligonucleotide fragments dictate which genomic regions will be labeled with which fluorophores.

There is no requirement for blocks of genomic regions to be painted in one color to be in one contiguous region. A single chromosome can be labeled as desired, in different colors, (e.g., up to 10 different colors), and at any position (e.g., up to 100 different positions). Patterns may include, but are not limited to, longitudinal or latitudinal stripes; solid transverse bands and lighter-colored interbands, "dots", overlapping segments, and repeats.

The lack of requirement for contiguous regions allows for the creation of new colors from standard fluorophores. As depicted in FIG. 1, neighboring probes may be labeled with different fluorophores 6, to provide different colors or different hues of similar colors 7. Thus, the labeled probes may be hybridized to target nucleic acids within fixed chromosomes to provide not only complex patterns which are not readily achievable by conventional methods, but also new colors generated by different combinations of fluorophores.

Accordingly, some of the features and advantages of certain embodiments of the subject methods include: 1) avoidance of non-specific amplification of starting materials, which leads to random amplification bias; 2) consistent creation of probes of a designated length (fragments generated in current PCR processes are often too long to be used effectively in FISH, requiring partial digestion by restriction enzymes that are difficult to control); 3) targeted chromosome "painting" on a very fine level such that microduplications, microinversions and microdeletions can be detected (current techniques allow for painting of chromosomes in sections, however, the smallest unit that can be painted in one color is 10 megabases (10 mB)); and 4) utilization of standard laboratory equipment for the visual detection of signals such that special filters, software and processing steps are not required.

Thus, the instant method provides a method in which a single chromosomal region can be labeled with more than one color. For example, additional labels can be used to give more colors, e.g., 3 labels gives 7 distinguishable signals (the three individual colors, three combinations of two colors, and one combination of all three colors), four labels gives 15 distinguishable signals, and so on.

Detectable labels suitable for use in the present method, compositions and kits include any label detectable by spectroscopic, photochemical, biochemical, immunochemical, electrical, optical or chemical means. Useful labels include biotin for staining with labeled streptavidin conjugate, magnetic beads (e.g., DYNABEADS), fluorescent dyes (e.g., fluorescein, TEXAS RED, rhodamine, green fluorescent protein, cyanins and the like), radiolabels (e.g., 3H, 35S, 14C, or 32P, enzymes (e.g., horseradish peroxidase, alkaline phosphatase and others commonly used in ELISA), and calorimetric labels such as colloidal gold or colored glass or plastic (e.g., polystyrene, polypropylene, latex, etc.) beads. Patents teaching the use of such labels include U.S. Pat. Nos. 3,817, 837; 3,850,752; 3,939,350; 3,996,345; 4,277,437; 4,275,149; and 4,366,241, which are herein incorporated by reference.

As noted above, an optically detectable signature refers to a light signal that can be detected by a fluorescence microscope, for example. An optically detectable signature may be made up of one or more signals, where the signal is produced by a label. An optically detectable signature includes: a single signal, a combination of two or more signals, ratio of magnitude of signals, etc. The signal may be visible light of a particular wavelength. An optically detectable signature may be provided by a fluorescent signal(s).

When more than one label is used, fluorescent moieties that emit different signal can be chosen such that each label can be distinctly visualized and quantitated. For example, a combination of the following fluorophores may be used: 7-amino-4-methylcoumarin-3-acetic acid (AMCA), TEXAS RED (Molecular Probes, Inc.), 5-(and-6)-carboxy-X-rhodamine, lissamine rhodamine B, 5-(and-6)-carboxyfluorescein, fluorescein-5-isothiocyanate (FITC), 7-diethylaminocoumarin-3-carboxylic acid, tetramethylrhodamine-5-(and-6)-isothiocyanate, 5-(and-6)-carboxytetramethylrhodamine, 7-hydroxycoumarin-3-carboxylic acid, 6-[fluorescein 5-(and-6)-carboxamido]hexanoic acid, N-(4,4-difluoro-5,7-dimethyl-4-bora-3a,4a diaza-3-indacenepropionic acid, eosin-5-isothiocyanate, erythrosin-5-isothiocyanate, and CASCADE BLUE acetylazide (Molecular Probes, Inc.). Hybridized oligonucleotides can be viewed with a fluorescence microscope and an appropriate filter for each fluorophore, or by using dual or triple band-pass filter sets to observe multiple fluorophores. See, e.g., U.S. Pat. No. 5,776, 688.

While the methods are not so limited, methods for combinatorial labeling are described in, e.g., see, Ried et al., 1992, *Proc. Natl. Acad. Sci. USA* 89, 1388-1392; Tanke, H. J. et al., 1999, *Eur. J. Hum. Genet.* 7:2-11. By using combined binary ratio labeling (COBRA) in conjunction with highly discriminating optical filters and appropriate software, over 40 signals can be distinguished in the same sample, see, e.g., Wiegant, J. et al., 2000, *Genome Research*, 10(6):861-865 (48-color FISH is feasible and more FISH colors may be generated using fewer primary fluorophores); Szuhai, K. et al., 2006, *Nat. Protoc.* 1(1):264-75 (staining of all 24 human chromosomes is accomplished with only four fluorochromes); Karhu, R. et al., 2001, *Genes Chromosomes Cancer*, 30(1): 105-9 (discussion of 42-color multicolor FISH technique permitting detection of chromosomal aberrations the resolution of chromosome arms); Rapp et al., 2006, *Cytogenet Genome Res.* 114:222-226 (review of practice and applications of COBRA-FISH).

Hybridized oligonucleotides also can be labeled with biotin, or digoxygenin, although secondary detection molecules or further processing may then be required to visualize the hybridized oligonucleotides and quantify the amount of hybridization. For example, an oligonucleotide labeled with biotin can be detected and quantitated using avidin conjugated to a detectable enzymatic marker such as alkaline phosphatase or horseradish peroxidase. Enzymatic markers can be detected and quantitated in standard colorimetric reactions using a substrate and/or a catalyst for the enzyme. Catalysts for alkaline phosphatase include 5-bromo-4-chloro-3-indolylphosphate and nitro blue tetrazolium. Diaminobenzoate can be used as a catalyst for horseradish peroxidase.

Prior to in situ hybridization, the oligonucleotides may be denatured. Denaturation is typically performed by incubating in the presence of high pH, heat (e.g., temperatures from about 70° C. to about 95° C.), organic solvents such as formamide and tetraalkylammonium halides, or combinations thereof.

Intact chromosomes are contacted with labeled amplification products under in situ hybridizing conditions. "In situ hybridizing conditions" are conditions that facilitate annealing between a nucleic aid and the complementary nucleic acid in the intact chromosomes. Hybridization conditions vary, depending on the concentrations, base compositions, complexities, and lengths of the probes, as well as salt concentrations, temperatures, and length of incubation. For example, in situ hybridizations may be performed in hybridization buffer containing 1-2×SSC, 50% formamide, and blocking DNA to suppress non-specific hybridization. In general, hybridization conditions include temperatures of about 25° C. to about 55° C., and incubation times of about 0.5 hours to about 96 hours. Suitable hybridization conditions for a set of oligonucleotides and chromosomal target can be determined via experimentation which is routine for one of skill in the art.

The contacted sample can be read using a variety of different techniques, such as, for example, by microscopy, flow cytometry, fluorimetry, etc. Microscopy, such as, for example light microscopy, fluorescent microscopy or confocal microscopy, is an established analytical tool for detecting light signal(s) from a sample. In embodiments in which oligonucleotides are labeled with a fluorescent moiety, reading of the contacted sample to detect hybridization of labeled amplification products may be carried out by fluorescence microscopy. Fluorescent microscopy or confocal microscopy used in conjunction with fluorescent microscopy has an added advantage of distinguishing multiple labels even when the labels overlap spatially.

In certain embodiments, the label is a fluorescent dye. Fluorescent dyes (fluorophores) suitable for use as labels in the present method can be selected from any of the many dyes suitable for use in imaging applications, especially flow cytometry. A large number of dyes are commercially available from a variety of sources, such as, for example, Molecular Probes (Eugene, Oreg.) and Exciton (Dayton, Ohio), that provide great flexibility in selecting a set of dyes having the desired spectral properties. Examples of fluorophores include, but are not limited to, 4-acetamido-4'-isothiocyanatostilbene-2,2'disulfonic acid; acridine and derivatives such as acridine, acridine orange, acridine yellow, acridine red, and acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate (Lucifer Yellow VS); N-(4-amino-1-naphthyl)maleimide; anthranilamide; Brilliant Yellow; coumarin and derivatives such as coumarin, 7-amino-4-methylcoumarin (AMC, Coumarin 120), 7-amino-4-trifluoromethylcouluarin (Coumaran 151); cyanine and derivatives such as cyanosine, Cy3, Cy5, Cy5.5, and Cy7; 4',6-diaminidino-2-phenylindole (DAPI); 5',5''-dibromopyrogallol-sulfonephthalein (Bromopyrogallol Red); 7-diethylamino-3-(4'-isothiocyanatophenyl)-4-methylcoumarin; diethylaminocoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein isothiocyanate (FITC), fluorescein chlorotriazinyl, naphthofluorescein, and QFITC (XRITC); fluorescamine; IR144; IR1446; Lissamine™; Lissamine rhodamine, Lucifer yellow; Malachite Green isothiocyanate; 4-methylumbelliferone; ortho cresolphthalein; nitrotyrosine; pararosaniline; Nile Red; Oregon Green; Phenol Red; B-phycoerythrin; o-phthaldialdehyde; pyrene and derivatives such as pyrene, pyrene butyrate and succinimidyl 1-pyrene butyrate; Reactive Red 4 (Cibacron™ Brilliant Red 3B-A); rhodamine and derivatives such as 6-carboxy-X-rhodamine (ROX), 6-carboxyrhodamine (R6G), 4,7-dichlororhodamine lissamine, rhodamine B sulfonyl chloride, rhodamine (Rhod), rhodamine B, rhodamine 123, rhodamine X isothiocyanate, sulforhodamine B, sulforhodamine 101, sulfonyl chloride derivative of sulforhodamine 101 (TEXAS RED), N,N,N',N'-tetramethyl-6-carboxyrhodamine (TAMRA), tetramethyl rhodamine, and tetramethyl rhodamine isothiocyanate (TRITC); riboflavin; rosolic acid and terbium chelate derivatives; xanthene; Alexa-Fluor dyes (e.g., Alexa Fluor 350, Alexa Fluor 430, Alexa Fluor 488, Alexa Fluor 546, Alexa Fluor 555, Alexa Fluor 568, Alexa Fluor 594, Alexa Fluor 633, Alexa Fluor 647, Alexa Fluor 660, Alexa Fluor 680, Alexa Fluor 700, Alexa Fluor 750), Pacific Blue, Pacific Orange, Cascade Blue, Cascade Yellow; Quantum Dot dyes (Quantum Dot Corporation); Dylight dyes from Pierce (Rockford, Ill.), including Dylight 800, Dylight 680, Dylight 649, Dylight 633, Dylight 549, Dylight 488, Dylight 405; or combinations thereof. Other fluorophores or combinations thereof known to those skilled in the art may also be used, for example those available from Molecular Probes (Eugene, Oreg.) and Exciton (Dayton, Ohio). Quantum dots may also be employed.

Fluorescence of a hybridized chromosome can be evaluated using a fluorescent microscope. In general, excitation radiation, from an excitation source having a first wavelength, passes through excitation optics. The excitation optics causes the excitation radiation to excite the sample. In response, fluorescent molecules in the sample emit radiation that has a wavelength that is different from the excitation wavelength. Collection optics then collects the emission from the sample. The device can include a temperature controller to maintain the sample at a specific temperature while it is being scanned. A multi-axis translation stage moves a microtiter plate holding a plurality of samples in order to position different wells to be exposed. The multi-axis translation stage, temperature controller, auto-focusing feature, and electronics associated with imaging and data collection can be managed by an appropriately programmed digital computer. The computer also can transform the data collected during the assay into another format for presentation. In general, known robotic systems and components can be used.

Table 1 below provides exemplary combinations of fluorophores that may be used together in combinations of 2, 3 or 4. This table is by no means comprehensive. In Table 1, 20 different 2 dye combinations, 9 different 3 dye combinations, and 8 different 4 dye combinations are denoted (read vertically; filled-in black box indicates dyes in the combination).

TABLE 1

Exemplary Dye Combinations (AF = Alexa Fluor).

| Fluorphore | 2 Dyes | 3 Dyes | 4 Dyes |
|---|---|---|---|
| Pacific Blue | | | |
| Pacific Orange | | | |
| AF 350 | | | |
| AF 488 (FITC) | | | |
| AF 594 | | | |
| AF 647 (Cy5) | | | |
| AF 700 (Cy5.5) | | | |
| AF 750 (Cy7) | | | |

In general, cytogenetic data may be produced by any convenient method. In one embodiment, the staining method employed is a multicolor FISH-based method that allows the visualization of all 24 autosomes, each in a different color. Such "chromosome painting" approaches are reviewed in Speicher et al. (*Nature Reviews* (2005) 6: 782-792), Liehr et al. (*Histol. Histopathol.* (2004) 19:229-37) and Matthew et al. (*Methods Mol. Biol.* (2003) 220: 213-33) and include multiplex-FISH (M-FISH; Speicher et al., *Nature Genet.* (1996) 12: 368-375), spectral karyotyping (SKY; Schrock et al., *Science* (1996) 273: 494-497) and combined binary ratio labeling (COBRA; Tanke et al., *Eur. J. Hum. Genet.* (1999) 7: 2-11). Such methods provide for identification of intrachromosomal rearrangements, and may be performed on genomic samples from non-dividing or metaphase cells, for example. All such methods may be readily adapted for use herein.

In general, the in situ hybridization methods used herein include the steps of fixing an intact chromosome to a support, hybridizing the labeled amplification products to target nucleic acids in the intact chromosome, and washing to remove non-specific binding. In situ hybridization assays and methods for sample preparation are well known to those of skill in the art and need not be described in detail here.

In certain embodiments, the binding pattern of the labeled amplification products to a chromosome may be compared with that of a reference chromosome. The reference chromosome may be from a supposedly healthy or wild-type organism. Briefly, the method comprises contacting under in situ hybridization conditions a test chromosome from the cellular sample with a plurality of strand-specific, fluorescently-labeled probes and contacting under in situ hybridization conditions a reference chromosome with the same plurality of strand-specific fluorescently-labeled probes. After hybridization, the emission spectra created from the unique binding patterns from the test chromosome are compared against those of the reference chromosome.

Thus, the structure of a test chromosome may be determined by comparing the pattern of binding of the labeled amplification products to the test chromosome with the binding pattern of the same labeled amplification products with a reference chromosome. The binding pattern of the reference chromosome may be determined before, after or at the same time as the binding pattern for the test chromosome. This determination may be carried out either manually or in an automated system. The binding pattern associated with the test chromosome can be compared to the binding pattern that would be expect for known deletions, insertions, translocation, fragile sites and other more complex rearrangements, and/or refined breakpoints. The matching may be performed by using computer-based analysis software known in the art. Determination of identity may be done manually (e.g., by viewing the data and comparing the signatures by hand), automatically (e.g., by employing data analysis software configured specifically to match optically detectable signature), or a combination thereof.

In another embodiment, the test sample is from an organism suspected to have cancer and the reference sample may comprise a negative control (non-cancerous) representing wild-type genomes and second test sample (or a positive control) representing a cancer associated with a known chromosomal rearrangement. In this embodiment, comparison of all these samples with each other using the subject method may reveal not only if the test sample yields a result that is different from the wild-type genome but also if the test sample may have the same or similar genomic rearrangements as another cancer test sample.

In certain embodiments, the subject method includes a step of transmitting data from at least one of the detecting and deriving steps, as described above, to a remote location. By "remote location" is meant a location other than the location at which the array is present and hybridization occur. For example, a remote location could be another location (e.g., office, lab, etc.) in the same city, another location in a different city, another location in a different state, another location in a different country, etc. As such, when one item is indicated as being "remote" from another, what is meant is that the two items are at least in different buildings, and may be at least one mile, ten miles, or at least one hundred miles apart. "Communicating" information means transmitting the data representing that information as electrical signals over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data. The data may be transmitted to the remote location for further evaluation and/or use. Any convenient telecommunications means may be employed for transmitting the data, e.g., facsimile, modem, internet, etc.

Kits

Also provided by the subject invention are kits for practicing the subject method, as described above. The subject kit contains a subject oligonucleotide composition and, in certain cases, a plurality of pairs of PCR primers, where each pair of PCR primers amplifies the variable region from a different set of oligonucleotides. The kit may further contain a polymerase, reagents for PCR (e.g., a buffer, nucleotides, etc), materials for fluorescent labeling of polymerase products, and a reference sample to be employed in the subject method. The various components of the kit may be in separate vessels.

In addition to above-mentioned components, the subject kit may further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Utility

The subject method finds use in a variety of applications, where such applications generally include genomic DNA analysis applications in which the presence of a particular chromosomal rearrangement in a given sample is to be detected. The subject methods may also be used to finely map chromosomal breakpoints, and other aberrations, such as micro-inversions, deletions and translocations without a priori knowledge of their location.

In general, the methods involve the use of a set of labeled probes designed to anneal to a target chromosome, giving multi-color-coding at high density. The chromosome under study, which may or may not be suspected of containing a chromosomal rearrangement, is contacted with strand-specific labeled probes. After hybridization, the binding pattern of the probes is analyzed, as described above.

Specific analyte detection applications of interest include but are not limited to chromosomal rearrangements and aberrations. One embodiment of the genomic analysis assay allows the detection of a chromosome inversion. In this embodiment, the assay contacts probes specific for a region of a reference chromosomal region under in situ hybridization conditions. If the test chromosomal region contains an inverted chromosomal segment that is visualized by a specific alteration in the characteristic emission spectra, an inversion has occurred. Matching the location of a probe to a database may provide the nucleotide sequence information of the probe hybridized to the test chromosome. Using the sequence information, the detailed location of the inversion junction may be deciphered.

The subject methods also find utility in the detection of chromosomal translocations. In this embodiment, the assay contacts probes specific for a region of a reference chromosomal region under in situ hybridization conditions. If the test chromosomal region contains newly juxtaposed segments from distant chromosomal regions that are visualized by their characteristic emission spectra, a translocation or complex chromosomal aberration has occurred. Again, sequence information from a database describing the starting probes can be used to decipher the location of the translocation junction.

The subject methods find use in a variety of diagnostic and research purposes since chromosomal inversions and translocations play an important role in conditions relevant to human diseases and genomic evolution of many organisms.

In particular, the above-described methods may be employed to diagnose, or investigate various types of genetic abnormalities, cancer or other mammalian diseases, including but not limited to, leukemia; breast carcinoma; prostate cancer; Alzheimer's disease; Parkinson's disease; epilepsy; amyotrophic lateral sclerosis; multiple sclerosis; stroke; autism; Cri du chat (truncation on the short arm on chromosome 5), 1p36 deletion syndrome (loss of part of the short arm of chromosome 1), Angelman syndrome (loss of part of the long arm of chromosome 15); Prader-Willi syndrome (loss of part of the short arm of chromosome 15); acute lymphoblastic leukemia and more specifically, chronic myelogenous leukemia (translocation between chromosomes 9 and 22); Velocardiofacial syndrome (loss of part of the long arm of chromosome 22); Turner syndrome (single X chromosome); Klinefelter syndrome (an extra X chromosome); Edwards syndrome (trisomy of chromosome 18); Down syndrome (trisomy of chromosome 21); Patau syndrome (trisomy of chromosome 13); and trisomies 8, 9 and 16, which generally do not survive to birth.

The disease may be genetically inherited (germline mutation) or sporadic (somatic mutation). Many exemplary chromosomal rearrangements discussed herein are associated with and are thought to be a factor in producing these disorders. Knowing the type and the location of the chromosomal rearrangement may greatly aid the diagnosis, prognosis, and understanding of various mammalian diseases.

Certain of the above-described methods can also be used to detect diseased cells more easily than standard cytogenetic methods, which require dividing cells and require labor and time-intensive manual preparation and analysis of the slides by a technologist. The above-described methods do not require living cells and can be quantified automatically since a computer can be programmed to count the number and/or arrangement of fluorescent dots present.

The above-described methods can also be used to compare the genomes of two biological species in order to deduce evolutionary relationships.

Chromosomes may be isolated from a variety of sources, including tissue culture cells and mammalian subjects, e.g., human, primate, mouse or rat subjects. For example, chromosomes may be analyzed from less than five milliliters (mL) of peripheral blood. White blood cells contain chromosomes while red blood cells do not. Blood may be collected and combined with an anti-clotting agent such as sodium heparin. Chromosomes may also be analyzed from amniotic fluid, which contains fetal cells. Such cells can be grown in tissue culture so that dividing cells are available for chromosomal analysis within 5-10 days. Chromosomes may also be analyzed from bone marrow, which is useful for diagnosis of leukemia or other bone marrow cancers. Chromosomes may also be analyzed from solid tissue samples. A skin or other tissue biopsy in the range of about 2-3 mm may be obtained aseptically and transferred to a sterile vial containing sterile saline or tissue transport media to provide material for chromosome analysis. Fetal tissue obtained after a miscarriage can also be used for chromosome analysis, such as from the fetal side of the placenta, the periosteum overlying the sternum or fascia above the inguinal ligament, or from chorionic villi. Fetal tissue can also be collected from multiple sites such as the kidneys, thymus, lungs, diaphragm, muscles, tendons, and gonads. An amniocentesis may also be performed.

In addition to the above, the instant methods may also be performed on bone marrow smears, blood smears, paraffin embedded tissue preparations, enzymatically dissociated tissue samples, uncultured bone marrow, uncultured amniocytes and cytospin preparations, for example.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. An oligonucleotide composition comprising:
a mixture of at least 2 sets of oligonucleotides,
wherein each of said sets of oligonucleotides comprises at least 10 different oligonucleotides of the following formula:

$$X_1-V-X_2, \text{wherein:}$$

$X_i$ and $X_2$ provide binding sites for a pair of PCR primers;
V is a variable region that has a variable nucleotide sequence that is complementary to one or more regions of a mammalian genome;
the nucleotide sequence of $X_1$ is the same for each oligonucleotide of a set and different for oligonucleotides of different sets;
the nucleotide sequence of $X_2$ is the same for each oligonucleotide of a set and different for oligonucleotides of different sets; and the variable regions of each set are complementary to a plurality of different regions of said mammalian genome.

2. The oligonucleotide composition of claim 1, wherein said mixture comprises at least 10 sets of oligonucleotides.

3. The oligonucleotide composition of claim 1, wherein each set comprises at least 1000 different oligonucleotides.

4. The oligonucleotide composition of claim 1, wherein, within a given set of oligonucleotides, the variable regions are complementary non-overlapping regions of a single chromosome.

5. The oligonucleotide composition of claim 1, wherein, within a given set of oligonucleotides: a) at least some of the variable regions are complementary to one or more discrete regions of a first chromosome of said mammalian genome and b) at least some of the variable regions are complementary to one of more discrete regions on a second, different, chromosome of said mammalian genome.

6. The oligonucleotide composition of claim 1, wherein said oligonucleotides are 100-200 nucleotides in length.

7. The oligonucleotide composition of claim 1, wherein said binding sites are 15-30 nucleotides in length.

8. The oligonucleotide composition of claim 1, wherein said variable region is 30-60 nucleotides in length.

9. The oligonucleotide composition of claim 1, wherein said oligonucleotides are in solution.

10. The oligonucleotide composition of claim 1, wherein said composition is made by fabricating an array of said oligonucleotides using in situ synthesis methods; and cleaving oligonucleotides from said array.

11. A labeling method comprising:
a) contacting a composition comprising a mixture of at least 2 sets of oligonucleotides,
wherein each of said sets of oligonucleotides comprises at least 10 different oligonucleotides of the following formula:

$X_1$—V—$X_2$, wherein:

$X_1$ and $X_2$ provide binding sites for a pair of PCR primers;
V is a variable region that has a variable nucleotide sequence that is complementary to one or more regions of a mammalian genome;
the nucleotide sequence of $X_1$ is the same for each oligonucleotide of a set and different for oligonucleotides of different sets;
the nucleotide sequence of $X_2$ is the same for each oligonucleotide of a set and different for oligonucleotides of different sets; and
the variable regions of each set are complementary to a plurality of different regions of said mammalian genome;
with a first pair of PCR primers under PCR conditions to provide a first set of amplification products, wherein said amplification products comprise the variable regions of a first set of oligonucleotides; and b) labeling said amplification products with a first label to provide first labeled amplification products.

12. The method of claim 11, further comprising contacting the composition with a second pair of PCR primers under PCR conditions to provide a second set of amplification products, wherein said amplification products comprise the variable regions of a second set of oligonucleotides; and
labeling said amplification products with a second label to provide second labeled amplification products.

13. The method of claim 12, further comprising contacting said first and second amplification products with an intact chromosome under hybridization conditions to provide a contacted chromosome.

14. The method of claim 13, further comprising imaging said contacted chromosome to provide an oligonucleotide binding pattern.

15. The method of claim 14, further comprising comparing said oligonucleotide binding pattern to a reference binding pattern to identify a chromosomal rearrangement.

16. The method of claim 11, wherein said labeled amplification products emit a signal that identifies the amplified variable regions.

17. The method of claim 13, wherein said first labeled amplification products and said second labeled hybridization products hybridize to the same region of a chromosome to produce a composite signal that indicates the identity of said region.

18. A kit comprising
a) an oligonucleotide composition comprising a mixture of at least 2 sets of oligonucleotides,
wherein each of said sets of oligonucleotides comprises at least 10 different oligonucleotides of the following formula:

$X_1$—V—$X_2$, wherein:

$X_1$ and $X_2$ provide binding sites for pair of PCR primers;
V is a variable region that has a variable nucleotide sequence that is complementary to one or more regions of a mammalian genome;
the nucleotide sequence of $X_1$ is the same for each oligonucleotide of a set and different for oligonucleotides of different sets;
the nucleotide sequence of $X_2$ is the same for each oligonucleotide of a set and different for oligonucleotides of different sets; and
the variable regions of each set are complementary to a plurality of different regions of said mammalian genome; and
b) a plurality of pairs of PCR primers, wherein each pair of PCR primers amplifies the variable region from a different set of oligonucleotides to produce amplification products.

19. The kit of claim 18, further comprising labeling reagents for labeling said amplification products.

* * * * *

UNITED STATES PATENT AND TRADEMARK OFFICE
CERTIFICATE OF CORRECTION

| | | |
|---|---|---|
| PATENT NO. | : 8,034,917 B2 | Page 1 of 1 |
| APPLICATION NO. | : 12/200675 | |
| DATED | : October 11, 2011 | |
| INVENTOR(S) | : N. Alice Yamada | |

It is certified that error appears in the above-identified patent and that said Letters Patent is hereby corrected as shown below:

IN THE CLAIMS:

In column 18, line 58, in Claim 1, delete "Xi" and insert -- X1 --, therefor.

In column 20, line 35, in Claim 18, delete "for pair" and insert -- for a pair --, therefor.

Signed and Sealed this
Thirteenth Day of March, 2012

David J. Kappos
*Director of the United States Patent and Trademark Office*